United States Patent [19]
Kim et al.

[11] Patent Number: 5,266,612
[45] Date of Patent: Nov. 30, 1993

[54] IMIDE EPOXY RESIN COMPOSITION FOR SEALING SEMICONDUCTOR ELEMENTS

[75] Inventors: Whan G. Kim; Ji Y. Lee, both of Seoul, Rep. of Korea

[73] Assignee: Cheil Industries, Inc., Rep. of Korea

[21] Appl. No.: 1,082

[22] Filed: Jan. 6, 1993

[30] Foreign Application Priority Data

Jan. 18, 1992 [KR] Rep. of Korea .................. 92-704

[51] Int. Cl.$^5$ ............... C08G 59/26; C08G 59/32; C08G 73/06; C08G 73/10
[52] U.S. Cl. .................... 523/443; 523/466; 525/476; 525/481; 525/482; 525/484; 525/485; 525/486; 525/487; 525/488; 528/96; 549/551; 549/553
[58] Field of Search ............... 523/443, 466; 525/481, 525/482, 484, 476, 485, 486, 487, 488; 528/96; 549/551, 553

[56] References Cited

U.S. PATENT DOCUMENTS 5,189,082  2/1993  Kim et al. ................... 525/481

FOREIGN PATENT DOCUMENTS

| | | |
|---|---|---|
| 54-142298 | 11/1979 | Japan . |
| 58-215452 | 12/1983 | Japan . |
| 62-477 | 1/1987 | Japan . |
| 62-7719 | 1/1987 | Japan . |
| 62-7723 | 1/1987 | Japan . |
| 62-106920 | 5/1987 | Japan . |
| 62-132961 | 6/1987 | Japan . |
| 62-260817 | 11/1987 | Japan . |
| 63-230725 | 9/1988 | Japan . |

*Primary Examiner*—Frederick Krass
*Attorney, Agent, or Firm*—Merchant, Gould, Smith, Edell, Welter & Schmidt

[57] ABSTRACT

An epoxy resin composition for sealing semiconductor elements comprising o-cresol-novolak type epoxy resins, curing agents, curing accelerators, inorganic fillers, plasticizers and imide-epoxy resins having the formula (I) is disclosed. Use of the imide-epoxy resin in an amount of 0.1 to 20.0% by weight improves the heat and moisture resistant properties of the epoxy resin composition.

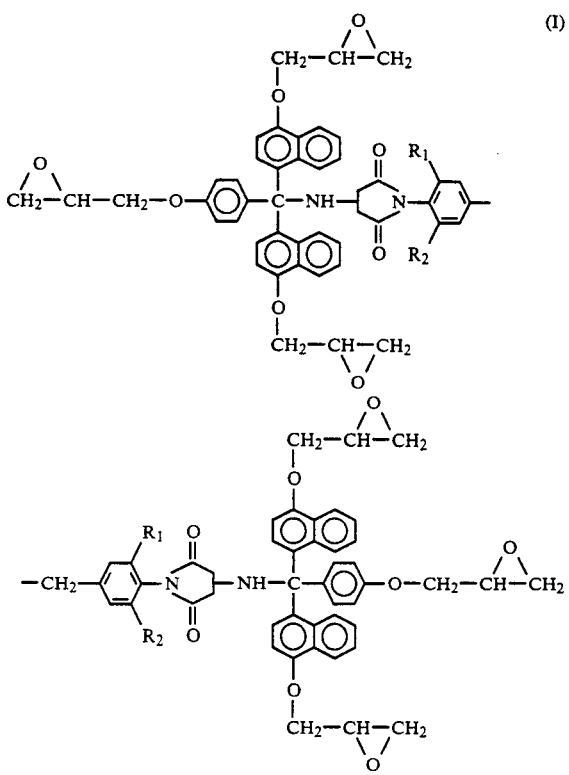

wherein,
$R_1$ and $R_2$ denote independently H or $(CH_2)nCH_3$ radical,
n denotes 0 or an integer of 1 above.

2 Claims, No Drawings

IMIDE EPOXY RESIN COMPOSITION FOR SEALING SEMICONDUCTOR ELEMENTS

FIELD OF THE INVENTION

The present invention relates to an epoxy resin composition for sealing semiconductor elements. More particularly, the present invention relates to an epoxy resin composition comprising an imide-epoxy resin in which an epoxy group is incorporated into bismaleimides to improve low stress, high heat resistance and high moisture resistance.

BACKGROUND OF THE INVENTION

Recently, owing to the tendency of electric and electronic components to be small and thin, IC and LSI packages are varied. Especially, while the size of a chip have become larger, the package have become thinner and varied with high pin numbers.

The mounting technology also varies to surface mounting technology. Recently, Thin Small Out-line J-Bend Packages (TSOJ) having a thickness of about 1 mm are being produced. TSOJ, which is a medium stage type between a Small Out-line J-Bend Packages (SOJ)/Quad Flat Package (QFP) and a Tape Automated Bonding (TAB), will be used as the main type of package in the memory element field in the near future.

The resin composition for sealing such semiconductor elements requires strict low stress, high heat and moisture resistant properties over the prior art compositions.

The method for decreasing inner stress by adding plasticizers such as a modified silicone oil or CTBN [Japanese Laid-open Patent Publication Nos. (Sho) 63-230725, 62-7723, 62-132961 and 62-260817] and the method for reducing the thermal expansion coefficient by increasing the amounts of fillers [Japanese Laid-open Patent Publication No. (Sho) 62-106920] are known as low stress techniques. However, such methods have serious problems such as low heat resistance, moldability and abrasion of equipments.

The method for improving heat resistance by using polyfunctional epoxy resins [Japanese Laid-open Patent Publication Nos. (Sho) 62-477, 62-7719 and 62-7723] and the method for increasing heat resistance by using a bismaleimide [Japanese Laid-open Patent Publication Nos. (Sho) 54-142298 and 58-215452] are well known. However, these methods have disadvantages in that due to an increase in the glass transition temperature of the resin composition the moisture resistant property decreases.

The purpose of the present invention is to provide an epoxy resin composition for sealing super thin type IC elements, with the use of an imide-epoxy resin in which epoxy radicals are introduced into the maleimide.

SUMMARY OF THE INVENTION

The present invention provides an epoxy resin composition comprising o-cresol-novolak type epoxy resins, phenol-novolak type curing agents, curing accelerators, and inorganic fillers and being useful for sealing semiconductor elements, which characterized in that an imide-epoxy resin represented by the formular (I) is incorporated thereto.

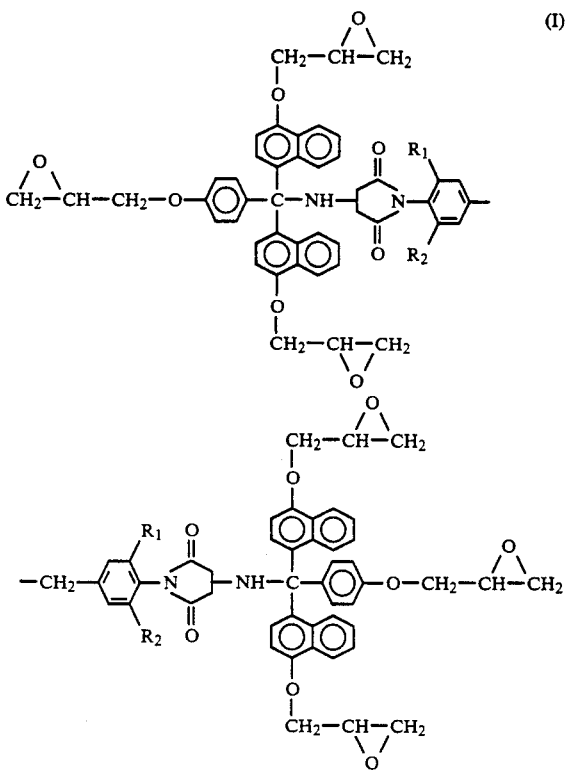

wherein,
$R_1$ and $R_2$ represent independently H or $(CH_2)nCH_3$ radical, and
n represents 0 or an integer of 1 or above.

DETAILED DESCRIPTION OF INVENTION

The use of an imide-epoxy resin represented by the formula (I) provides the resin composition of the present invention with improved low stress, high heat resistance and moisture resistance characteristics.

The imide-epoxy resin having the formula (I) of the present invention may be prepared by the following routes: An epoxy compound and benzoyl peroxide are dissolved in a non-polar organic solvent, to this mixture N-bromosuccinimide (NBS) is added with stirring under reflux, and then the mixture is purified to give a bromine-substituted epoxy resin. The resulting epoxy resin is dissolved in diethyl ether, reacted with alkoxyamine to obtain an amine-substituted epoxy resin, and finally reacted with maleimide.

The synthesis routes for preparing the imide-epoxy resin (I) of the present invention may be summarized by the following reaction procedures (1) to (3):

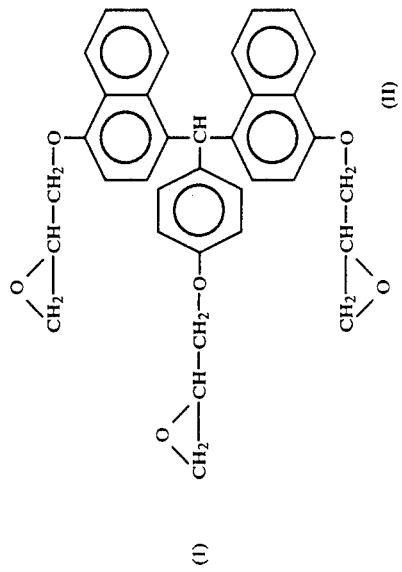
(I)
i) Benzoyl peroxide
ii) NBS
CCl₄ or C₂H₄Cl₂
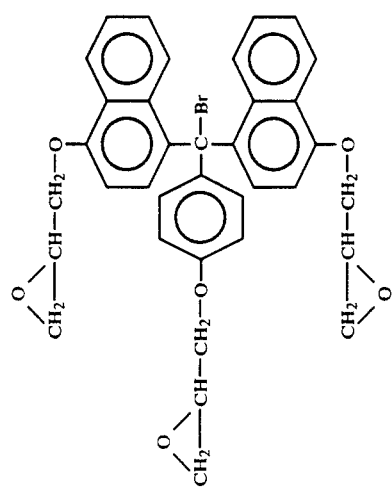
(II)
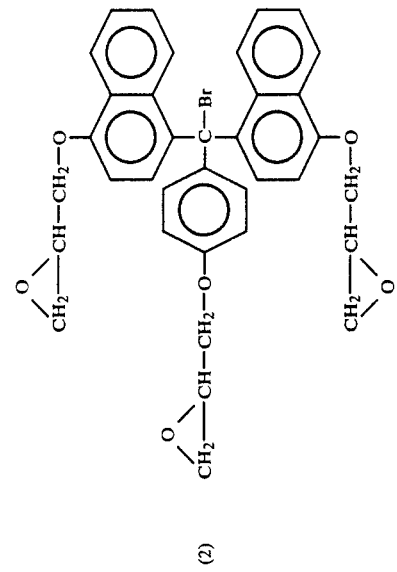
(2)
i) Mg
ii) o-methylhydroxylamine
Diethyl ether or THF
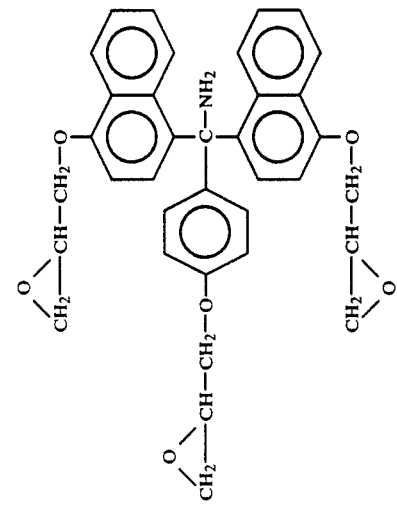

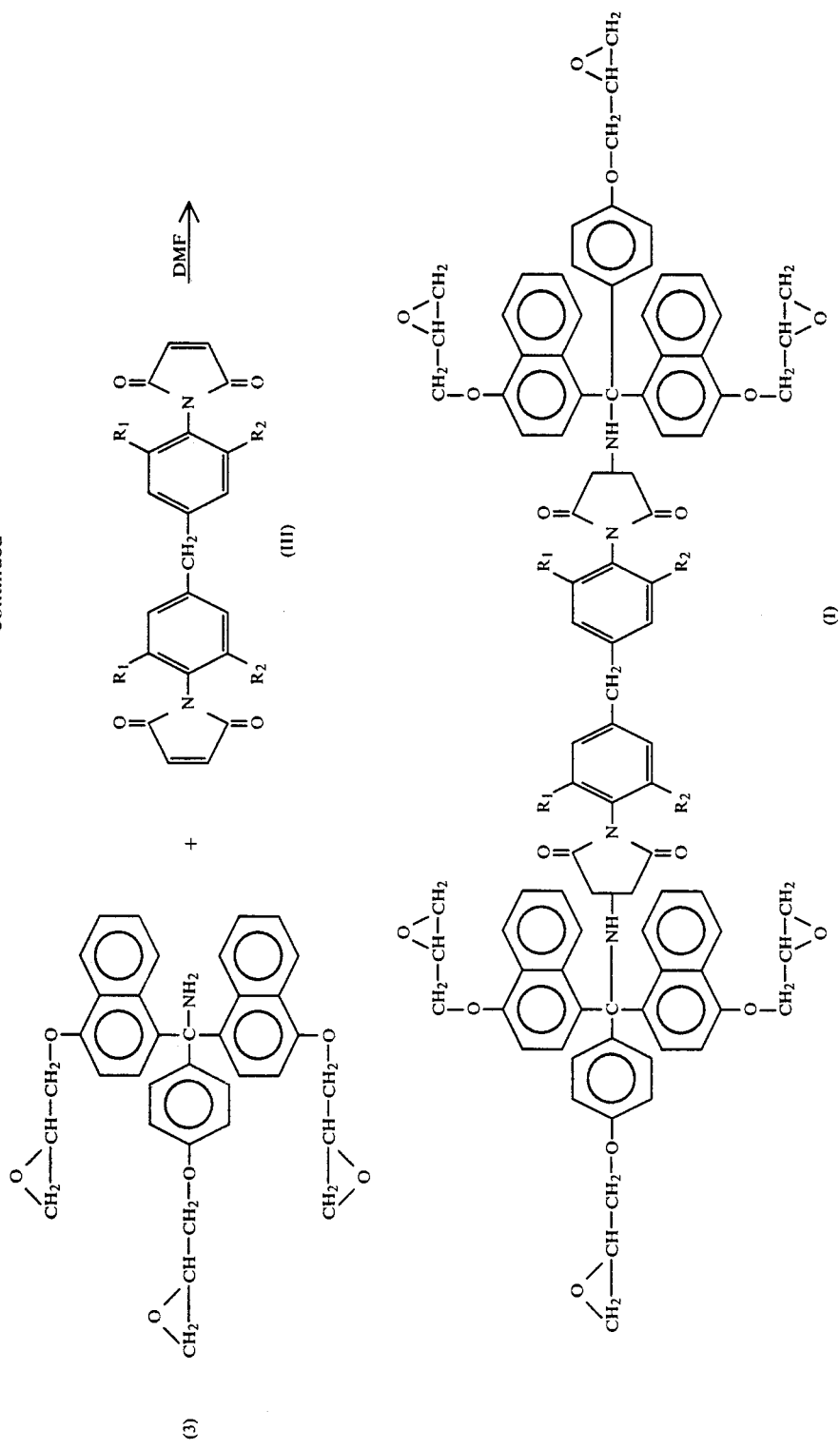

wherein, $R_1$ and $R_2$ have the same meaning as above.

Each of the reaction procedures (1) to (3) for preparing the imide-epoxy resin (I) can be described in detail as follows:

The epoxy compound having the formula (II) and benzoyl peroxide are dissolved in $CCl_4$ or $C_2H_4Cl_2$, to this mixture N-bromosuccinimide (NBS) is added dropwise with stirring under reflux for several hours, and then the mixture is purified to give a bromine-substituted epoxy compound [Reaction Procedure (1)].

The bromine substituted epoxy compound and magnesium metal are added to dry diethyl ether or tetrahydrofuran (THF). Upon completely dissolving them, to this mixture alkoxyamine such as o-methylhydroxylamine is added. The mixture is allowed to react for several hours, while keeping it warm in a bath. The resulting by-product is removed by the purification to give an amine-substituted epoxy compound [Reaction Procedure (2)].

The resulting epoxy compound is reacted with maleimide having the formular (III) in dimethyl formamide (DMF) for several hours to give an imide-epoxy resin having the formula (I) [Reaction Procedure (3)].

The imide-epoxy resin (I) is incorporated into the epoxy resin composition of the present invention in an amount of 0.1 to 20% by weight, based on the total weight of the resin composition.

The epoxy resin (II) includes a special grade epoxy resin available from Nippon Chemical Co.

The maleimide (III) used in preparing the imide-epoxy resin of the present invention includes MB 3000, MB 3000H, MB 7000, MP 256, MP 276, and the like, which are available from Mitsubishi Petrochemical Co., Ltd.

Other reactants and solvents are commercially available.

The epoxy resin composition of the present invention is based on the epoxy resin component obtained by mixing o-cresol-novolak type epoxy resin with the imide-epoxy resin (I). The epoxy resin of the present invention further includes a phenol-novolak type curing agent, a curing accelerator such as triphenylphosphine belonging to organic phosphine compounds, a filler such as high purity fused silica, a mold release agent, a colorant, and an organic or inorganic flame retardant.

The preferred constitutional example of the present epoxy resin composition is as follows:

| | |
|---|---|
| o-cresol-novolak type epoxy resin | 0.1–20.0% by weight |
| imide epoxy resin | 0.1–20.0% by weight |
| curing agent | 1.0–10.0% by weight |
| curing accelerator | 0.1–1.0% by weight |
| coupling agent | 0.5–2.0% by weight |
| colorant | 0.1–0.5% by weight |
| filler | 65.0–85.0% by weight |
| mold release agent | 0.1–1.0% by weight |
| organic flame retardant | 1.0–5.0% by weight |
| inorganic flame retardant | 0.5–3.0% by weight |
| plasticizer | 0.5–5.0% by weight |

The above resin composition is the most preferred for the resin composition of the present invention. The epoxy resin to be used in the present invention should be a good heat resistant o-cresol-novolak type resin, especially a high pure epoxy resin having 190 to 220 epoxy equivalent weight with an impurity content below 10 ppm. As to the curing agent, a phenol-novolak type resin, which has a softening point of 80° to 100° C., 100 to 120 hydroxyl equivalent weight and below 10 ppm impurity content, may be used.

High performance epoxy resin to be used specifically in the present invention includes imide-epoxy resin, and the amount to be used is preferably between 0.1 and 20.0% by weight, and more preferably between 1.0 and 10.0% by weight, based on the total weight of the resin composition.

If the amount to be used is less than 0.1% by weight, the heat and moisture resistance are very poor, and if the amount to be used is greater than 20% by weight, phenomena such as resin bleed and mold fouling occur. Thus, moldability decreases and problems related to the gel time and conditions at post-curing result.

It is preferable to use high purity fused silica as the filler in the resin composition of the present invention. Fused silica having a particle size of 10 to 30 μm is preferable.

Curing accelerator includes amines, imidazole derivatives and organic phosphine compounds being conventionally used. In the resin composition of the present invention, it is preferable to use triphenylphosphine, and 2-methylimidazole and 2-methyl-4-ethylimidazole as organic phosphine compounds and imidazole derivatives, respectively.

The coupling agent to be used in the surface treatment of inorganic fillers includes silane-based coupling agents. It is the most preferable to use γ-glycidoxy-propyltrimethoxysilane.

As plasticizers, silicone oil or epoxy-modified silicone oil is conventionally used. In the resin composition of the present invention, plasticizers are used to increase the compatibility according to the high integration of semiconductors, and include an adduct of phenol-novolak resins and epoxy-modified silicone oil.

The epoxy resin composition of the present invention may further comprise 0.1 to 1.0% by weight of carnauba wax or Montan wax as a mold release agent, 0.1 to 0.5% by weight of carbon black as a colorant, brominated epoxy resin as an organic flame retardant and antimony trioxide as an inorganic flame retardant.

The resin composition of the present invention can be prepared by surface treating inorganic fillers with coupling agents, homogeneously mixing them with the remaining components in Henschel mixer or other premixer, melt mixing the mixture at 90° to 110° C. for about 5 to 20 min. with kneader or roll mill, cooling and pulverizing.

The resultant powdery composition may then be tableted by a tableting machine. In use, the obtained resin composition tablet is preheated with a high frequency preheater, and molded with a molding press at 170° to 180° C. for 90 to 120 sec. to seal the semiconductor elements.

As mentioned above, since the resin composition prepared by the present invention includes an imide-epoxy resin, in addition to the conventional cresol-novolak type epoxy resin, it has high glass transition temperature and improved moisture resistance, and thus, can provide a resin composition suitable for sealing super-thin, high integrated semiconductor elements.

Hereinafter, the present invention will be described in detail by means of examples, which should not be construed as limiting the scope of the present invention.

EXAMPLES 1–4

Constitutional components having the composition set forth in Table 1 are intimately mixed in Henschel mixer to give powdery composition. The powdery composition is kneaded for 10 min. at 100° C., cooled, and ground to give epoxy resin molding materials.

Physical properties of the resulting resin composition are measured with the following methods. The results are listed on Table 2:

1) Spiral flow: Measured at 175° C. of molding temperature and 70 kg. f/cm² of molding pressure with a mold prepared according to EMMI standard
2) Tg: Measured with TMA equipment
3) E(kg. f/mm²): Measured with UTM according to ASTM D 190
4) Thermal expansion coefficient α (°C$^{-1}$): Measured according to ASTM D 696
5) Moisture content (%): Measured the saturated moisture content, after standing the molded article for 48 hrs. in 121° C., 2 atm. vapor
6) Resistant to cracking: Measured from the crack numbers generated in the 2,000 times thermal impact test on the molded chip under the test conditions having one cycle of −55° C., 30 min. and 150° C., 30 min.

COMPARATIVE EXAMPLE

The same constitutional components as Examples 1 to 4 are used to prepare a resin composition except that the imide-epoxy resin of the present invention is not used. Physical properties thereof are listed in Table 2.

TABLE 1

(Unit: % by weight)

| Components | Example 1 | Example 2 | Example 3 | Example 4 | Comparative Example |
|---|---|---|---|---|---|
| Cresol-novolak type epoxy resin | 13.57 | 11.57 | 9.07 | 4.07 | 15.07 |
| Imide-epoxy resin (DDM-BMI based epoxy resin) | 1.5 | 3.5 | 6.0 | 11.0 | — |
| Phenol-novolak (curing agent) | 4.83 | 4.83 | 4.83 | 4.83 | 4.83 |
| Triphenylphosphine (curing accelerator) | 0.3 | 0.3 | 0.3 | 0.3 | 0.3 |
| Fused silica (filler) | 74.9 | 74.9 | 74.9 | 74.9 | 74.9 |
| Epoxy-modified silicone oil (plasticizer) | 1.0 | 1.0 | 1.0 | 1.0 | 1.0 |
| Brominated epoxy resin (organic flame retardant) | 1.45 | 1.45 | 1.45 | 1.45 | 1.45 |
| KBM 403* (coupling agent) | 1.21 | 1.21 | 1.21 | 1.21 | 1.21 |
| Carnauba wax (mold release agent) | 0.13 | 0.13 | 0.13 | 0.13 | 0.13 |
| Sb$_2$O$_3$ (inorganic flame retardant) | 0.85 | 0.85 | 0.85 | 0.85 | 0.85 |
| Carbon black (colorant) | 0.26 | 0.26 | 0.26 | 0.26 | 0.26 |

*available from Shin-Etsu Chemical

TABLE 2

| Contents | Example 1 | Example 2 | Example 3 | Example 4 | Comparative Example |
|---|---|---|---|---|---|
| Spiral flow (in.) | 45 | 46 | 43 | 43 | 45 |
| Tg (°C.) | 184 | 180 | 190 | 194 | 180 |
| α (× 10$^{-5}$/°C.) | 1.4 | 1.3 | 1.3 | 1.3 | 1.6 |
| E (kg. f/mm²) | 1250 | 1150 | 1200 | 1250 | 1200 |
| Moisture content (%) | 0.39 | 0.42 | 0.40 | 0.38 | 0.43 |
| Resistance to cracking *(2000 times) | 2/600 | 1/600 | 1/600 | 1/600 | 5/600 |

*Denominato represents the number of samples, and numerato represents the failure numbers.

As can be aware from the above Table 2, the epoxy resin composition of the present invention has good moldability and high heat and moisture resistance over the composition of the Comparative Example, and also improved resistance to cracking.

We claim:

1. An epoxy resin composition for sealing semiconductor elements comprising: an o-cresol-novolak epoxy resin, an imide-epoxy resin, a phenol-novolak curing agent, a triphenyl-phosphine curing accelerator promoter, and an inorganic filler, wherein the imide-epoxy resin is represented by the formula (I), as follows:

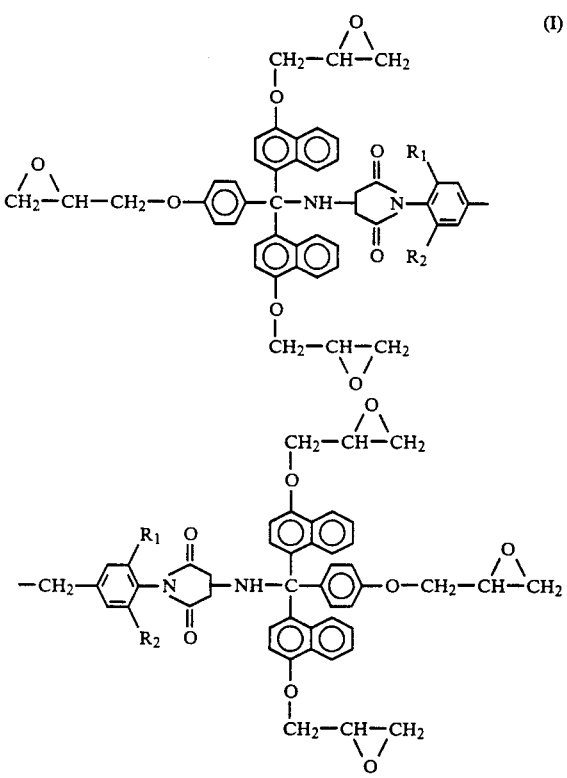

wherein, $R_1$ and $R_2$ denote independently, H or a-$(CH_2)_nCH_3$ radical, and n denotes 0 or an integer of 1 or above.

2. The epoxy resin composition according to claim 1, wherein the amount of the imide-epoxy resin is about 0.1 to 20.0% by weight, based on the total weight of the epoxy resin composition.

* * * * *